US00PP13054P2

(12) United States Plant Patent
Bergman et al.

(10) Patent No.: US PP13,054 P2
(45) Date of Patent: Oct. 8, 2002

(54) CHRYSANTHEMUM PLANT NAMED 'YOFIRE ISLAND'

(75) Inventors: Wendy R. Bergman, Lehigh Acres, FL (US); Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,843

(22) Filed: Sep. 20, 2001

(51) Int. Cl.[7] ..... A01H 5/00
(52) U.S. Cl. ..... Plt./286

(58) Field of Search ..... Plt./286

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yofire Island', characterized by its uniform and upright plant habit; strong and freely branching growth habit; dark green glossy foliage; uniform and freely flowering habit; early flowering, eight-week response time; large daisy-type inflorescences that are about 11.7 cm in diameter; red and yellow bi-colored ray florets; and good postproduction longevity with plants maintaining good substance and color for at least four weeks in an interior environment.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yofire Island'.

The new Chrysanthemum is a product of a planned breeding program conducted by the Inventors in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventors in October, 1994, in Salinas, Calif., of the Chrysanthemum cultivar Rage, disclosed in U.S. Plant Pat. No. 8,770, as the female, or seed, parent with a proprietary Chrysanthemum seedling selection identified as code number YB-5547, not patented, as the male, or pollen, parent. The new Chrysanthemum was discovered and selected by the Inventors as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in July, 1996. Asexual reproduction by cuttings has shown that the unique features of this new Chrysanthemum are stable and reproduced true to type in successive generations.

SUMMARY OF THE INVENTION

The cultivar Yofire Island has not been observed under all possible environmental conditions. The phenotype may vary somewhat with variations in environment such as temperature, daylength, and/or light level, wihout, however, any variance in genotype.

The following traits have been repeatedly observed and are determined to be the unique characteristics of 'Yofire Island'. These characteristics in combination distinguish 'Yofire Island' as a new and distinct Chrysanthemum:

1. Uniform and upright plant habit.
2. Strong and freely branching growth habit.
3. Dark green glossy foliage.
4. Uniform and freely flowering habit.
5. Can be grown as a disbud or spray-type.
6. Early flowering, eight-week response time.
7. Large daisy-type inflorescences that are about 11.7 cm in diameter.
8. Red and yellow bi-colored ray florets.
9. Good postproduction longevity with plants maintaining good substance and color for at least four weeks in an interior environment.

Plants of the new Chrysanthemum differ primarily from plants of the female parent selection in ray floret coloration as plants of the new Chrysanthemum have bright red and yellow bi-colored ray florets whereas plants of the female parent selection have solid bright red-colored ray florets.

Plants of the new Chrysanthemum differ primarily from plants of the male parent selection in ray floret coloration as plants of the new Chrysanthemum have bright red and yellow bi-colored ray florets whereas plants of the male parent selection have light pink-colored ray florets.

Plants of the new Chrysanthemum can be compared to plants of the cultivar Pelee, disclosed in U.S. Plant Pat. No. 8,464. In side-by-side comparisons conducted by the Inventors in Salinas, Calif., plants of the new Chrysanthemum differed from plants of the cultivar Pelee in the following characteristics:

1. Plants of the new Chrysanthemum had a more uniform plant habit and flowering response than plants of the cultivar Pelee.
2. Plants of the new Chrysanthemum had darker green foliage than plants of the cultivar Pelee.

3. Plants of the new Chrysanthemum flowered about four to five days earlier than plants of the cultivar Pelee.

Plants of the new Chrysanthemum can also be compared to plants of the cultivar Yococoa Beach, disclosed in U.S. Plant Pat. No. 12,317. In side-by-side comparisons conducted by the Inventors in Salinas, Calif., plants of the new Chrysanthemum differed from plants of the cultivar Yococoa Beach in the following characteristics:

1. Plants of the new Chrysanthemum had a more uniform plant habit than plants of the cultivar Yococoa Beach.

2. Ray floret color of plants of the new Chrysanthemum was brighter and more vivid than ray floret color of plants of the cultivar Yococoa Beach.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yofire Island' grown as a disbud-type.

The photograph on the second sheet comprises a close-up view of typical inflorescences of 'Yofire Island' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of pinching, the photoinductive short day/long night treatments were started. Plants used for this description were grown as disbud-types. Measurements and numerical values represent averages of typical flowering plants.

Botanical classification: *Chrysanthemum×morifolium* cultivar Yofire Island.

Commercial classification: Daisy-type potted Chrysanthemum.

Parentage:

*Female, or seed, parent.*—*Chrysanthemum×morifolium* cultivar Rage, disclosed in U.S. Plant Pat. No. 8,770.

*Male, or pollen, parent.*—Proprietary *Chrysanthemum×morifolium* seedling selection identified as code number YB-5547, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that can be grown as a disbud or as a spray-type. Stems mostly upright and somewhat outwardly spreading; uniform crown. Very freely branching, about five lateral branches develop after removal of terminal apex (pinching); dense and full plants.

*Plant height.*—About 32 cm.

*Plant width.*—About 38 cm.

*Lateral branches* (*peduncles*).—Length: About 26.5 cm. Diameter: About 5 mm. Internode length: About 2.1 cm. Strength: Strong. Texture: Pubescent. Color: 146A.

*Foliage description.*—Arrangement: Alternate. Quantity of leaves per lateral stem: About 11 or 12. Length: About 7.5 cm. Width: About 5.7 cm. Apex: Cuspidate to mucronate. Base: Attenuate to truncate. Margin: Palmately lobed, sinuses between lateral lobes divergent. Texture: Upper and lower surfaces with very fine pubescence; veins prominent on lower surface. Color: Young foliage, upper surface: Darker than 147A. Young foliage, lower surface: Darker than 147B. Mature foliage, upper surface: Close to 147A, glossy. Mature foliage, lower surface: Close to 147B. Venation, upper surface: Close to 147A. Venation, lower surface: 146B. Petiole length: About 2.3 cm. Petiole diameter: About 5 mm. Petiole color: Upper surface: Close to 146A. Lower surface: Close to 146B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 50 to 54 days later when grown as a disbud-type and about 54 to 58 days later when grown as a spay-type.

*Postproduction longevity.*—Inflorescences maintain good color and substance for at least four weeks in an interior environment.

*Quantity of inflorescences.*—Grown as a disbud-type, only one inflorescence, the terminal inflorescence, devolops per lateral branch.

*Inflorescence bud.*—Height: About 5 mm. Diameter: About 7 mm. Color: Close to 137A.

*Inflorescence size.*—Diameter: About 11.7 cm. Depth (height): About 3.2 cm. Diameter of disc: About 2 cm. Receptacle diameter: About 1 cm.

*Ray florets.*—Shape: Elongated-oblong. Orientation: Initially upright, then about 60 to 65° from vertical. Aspect: Mostly flat and straight. Length: About 5.5 cm. Width: About 1.2 cm. Apex: Acute or emarginate. Base: Attenuate; short corolla tube. Corolla tube length: About 5 mm. Margin: Entire. Texture: Smooth, glabrous, satiny. Number of ray florets per inflorescence: About 35 arranged in one or two rows. Color: When opening and fully expanded, upper surface: Ground color, yellow, 9A; overlain with red, 46A to 53A, mostly towards the apex and along central veins. When opening and fully expanded, lower surface: Ground color, yellow, 8A to 8B; faintly underlain with red, 53A, towards apex.

*Disc florets*.—Arrangement: Massed at center of receptacle. Shape: Tubular, elongated. Apex: Five-pointed. Length: About 8 mm. Width: Apex: About 1.5 mm. Base: About 1 mm. Number of disc florets per inflorescence: About 185. Color: Immature: 144A to 154A. Mature: Apex: 7A. Mid-section: Closest to 145C. Base: Closest to 155D.

*Reproductive organs*.—Androecium: Present on disc florets only. Anther color: 7A to 9A. Pollen amount: Moderate. Pollen color: 14A. Gynoecium: Present on both ray and disc florets.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yofire Island', as illustrated and described.

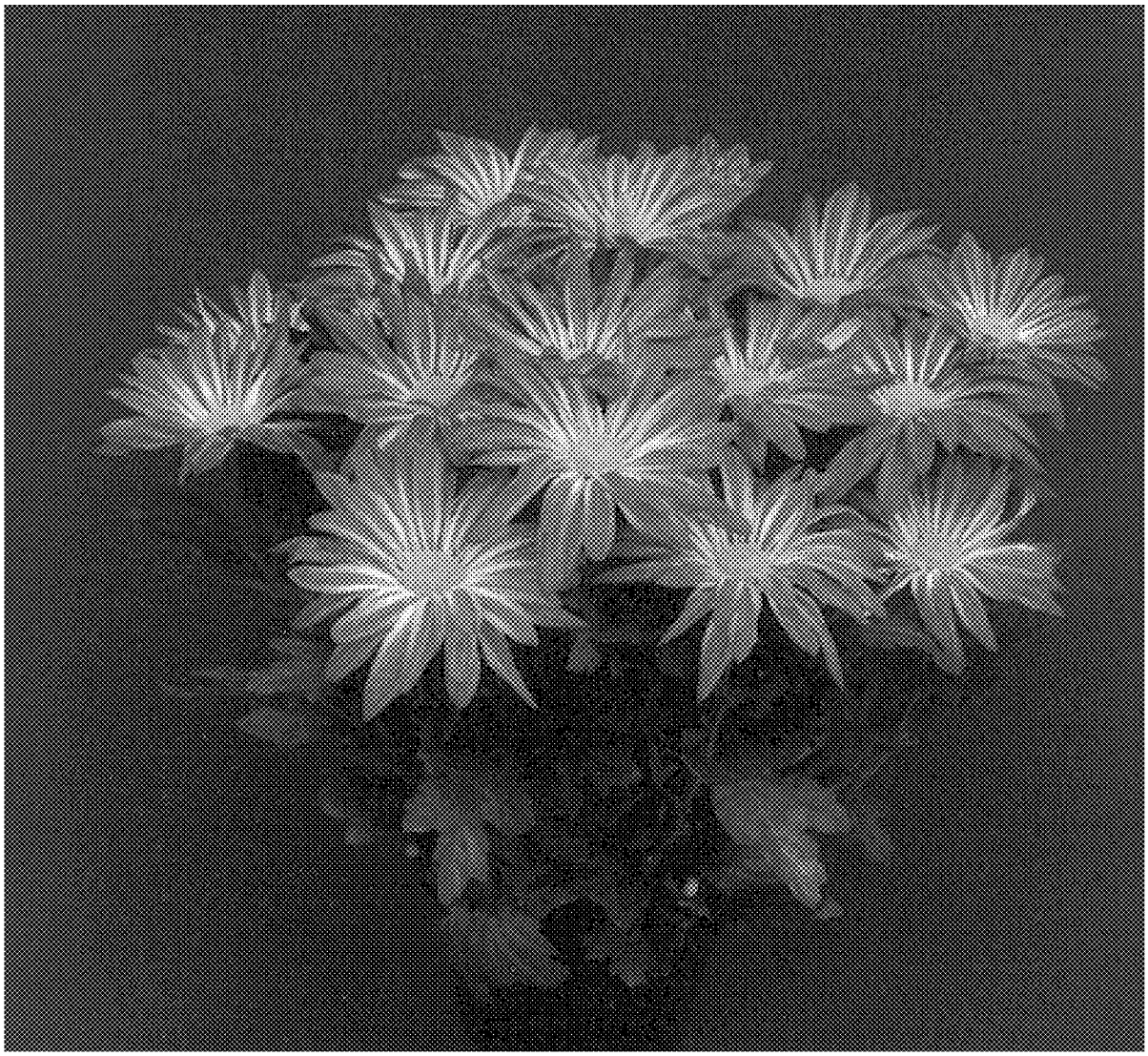

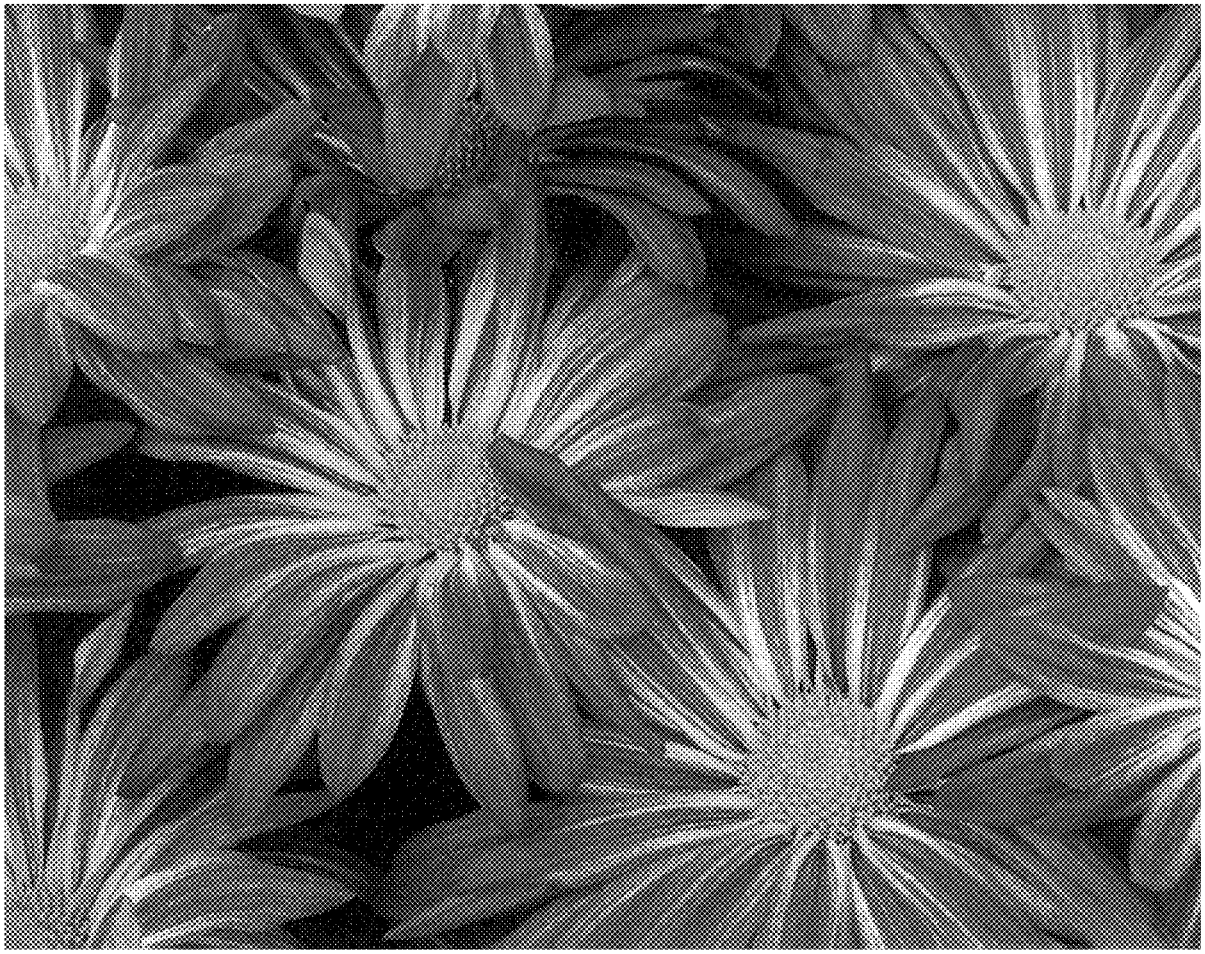

* * * * *